(12) United States Patent
Sekizawa et al.

(10) Patent No.: US 9,372,133 B2
(45) Date of Patent: Jun. 21, 2016

(54) MICROCHEMICAL CHIP, PRODUCING METHOD THEREOF AND METHOD FOR USING THE MICROCHEMICAL CHIP

(75) Inventors: Ryuichi Sekizawa, Kanagawa (JP); Ryoko Aso, Kanagawa (JP)

(73) Assignee: METABOSCREEN CO., LTD., Kanagawa (JP)

( * ) Notice: Subject to any disclaimer, the term of this patent is extended or adjusted under 35 U.S.C. 154(b) by 338 days.

(21) Appl. No.: 13/807,625

(22) PCT Filed: Jun. 29, 2011

(86) PCT No.: PCT/JP2011/003728
§ 371 (c)(1),
(2), (4) Date: Dec. 28, 2012

(87) PCT Pub. No.: WO2012/001972
PCT Pub. Date: Jan. 5, 2012

(65) Prior Publication Data
US 2013/0101993 A1    Apr. 25, 2013

(30) Foreign Application Priority Data
Jun. 30, 2010    (JP) .................................. 2010-149963

(51) Int. Cl.
*B01L 1/00*    (2006.01)
*G01N 35/00*    (2006.01)
(Continued)

(52) U.S. Cl.
CPC ............ *G01N 1/28* (2013.01); *B01L 3/502707* (2013.01); *B01L 2300/0803* (2013.01); *B01L 2300/0874* (2013.01);
(Continued)

(58) Field of Classification Search
CPC ............ B01L 3/5027; B01L 3/502707; B01L 2300/0887; B01L 2300/0874
See application file for complete search history.

(56) References Cited

U.S. PATENT DOCUMENTS 5,250,263 A * 10/1993 Manz .............................. 422/81
5,755,942 A *  5/1998 Zanzucchi et al. ............. 506/32
6,494,614 B1 * 12/2002 Bennett et al. ................ 366/336
(Continued)

FOREIGN PATENT DOCUMENTS

CN          1690692 A     11/2005
JP       2000-81406 A      3/2000
(Continued)

OTHER PUBLICATIONS

International Search Report for Application No. PCT/JP2011/003728, Jul. 26 2011, p. 1-2.
(Continued)

*Primary Examiner* — Nathan Bowers

(57) ABSTRACT

According to the microchemical chip of the present invention, the sample introducing port 11 is formed as a hole penetrating a face and a back of the first substrate 10, the sample flow path 21 is formed as a slit penetrating a face and a back of the second substrate 20, the sample discharging port 31 is formed as a hole penetrating a face and a back of the third substrate 30, the second substrate 20 is disposed between the first substrate 10 and the third substrate 30, the sample introducing port 11 and the sample discharging port 31 are in communication with each other through the sample flow path 21, and one of ends of the sample flow path 21 is an opening port, and thus, a square hollow groove including an angle having one piece of about 100 microns can be produced as the sample flow path 21.

14 Claims, 11 Drawing Sheets

(51) Int. Cl.
   *G01N 1/28*   (2006.01)
   *B01L 3/00*   (2006.01)

(52) U.S. Cl.
   CPC . *B01L 2300/0887* (2013.01); *B01L 2400/0406* (2013.01); *G01N 35/00069* (2013.01); *Y10T 156/1052* (2015.01)

(56) References Cited

U.S. PATENT DOCUMENTS

| | | | |
|---|---|---|---|
| 6,619,311 B2 * | 9/2003 | O'Connor et al. | 137/109 |
| 2002/0187560 A1 * | 12/2002 | Pezzuto et al. | 436/180 |
| 2003/0198130 A1 * | 10/2003 | Karp et al. | 366/341 |
| 2006/0057740 A1 | 3/2006 | Hiroshi | |
| 2007/0003444 A1 * | 1/2007 | Howell et al. | 422/100 |
| 2008/0207892 A1 | 8/2008 | Iwaki | |
| 2010/0233824 A1 | 9/2010 | Verhoeckx | |
| 2011/0301047 A1 * | 12/2011 | Immink | G01N 33/54373 506/7 |

FOREIGN PATENT DOCUMENTS

| | | |
|---|---|---|
| JP | 2000-093816 A | 4/2000 |
| JP | 2001-157855 A | 6/2001 |
| JP | 2002-515351 A | 5/2002 |
| JP | 2004-184180 A | 7/2004 |
| JP | 2005-000770 A | 1/2005 |
| JP | 2005-510695 A | 4/2005 |
| JP | 3116709 U | 12/2005 |
| JP | 2007-514142 A | 5/2007 |
| JP | 4073023 B2 | 4/2008 |
| JP | 2008-148690 A | 7/2008 |
| JP | 2008-200006 A | 9/2008 |
| WO | 03-045559 A2 | 6/2003 |
| WO | 2009/013658 A2 | 1/2009 |

OTHER PUBLICATIONS

The State Intellectual Property Office of the People's Republic of China (SIPO), Office Action for Chinese Patent Application No. 201180032599.1, Aug. 2014.

The State Intellectual Property Office of the People's Republic of China (SIPO), Search Report for Chinese Patent Application No. 201180032599.1, Aug. 2014.

* cited by examiner (a)

10  11

(b)

20  21

(c)

30  31

(d)

30 20 10 11

(e)

10 11 21

(f)

21h 21a  21b 21c 21g 21f  21e 21d
40

(g)

30 21a 20 10

(a)

(b)

(a)

(b)

(a)

(b)

10  20  30

(a)

(b)

(a)

(b)

(c)

(d)

(a)

(b)

(c)

(a)

(b)

(a)

(b)

(c)

(a)

(b)

(c)

(a)

(b)

MICROCHEMICAL CHIP, PRODUCING METHOD THEREOF AND METHOD FOR USING THE MICROCHEMICAL CHIP

TECHNICAL FIELD

The present invention relates to a microchemical chip capable of measuring a chemical/biochemical function of many items using a fine flow path formed on a substrate, a producing method of the microchemical chip, and a method for using the microchemical chip.

BACKGROUND TECHNIQUE

As a microchemical chip of this kind, there is already proposed one in which a penetrating flow path is formed therein, a capillary is embedded in at least a portion of the flow path, a dummy rod for closing the flow path is further embedded in the microchemical chip, the flow path is provided in a branch form or a lattice form, and the capillary is made of glass or plastic (patent document 1).

As another microchemical chip, there is also proposed one in which a plurality of grooves connected in parallel or in series are formed on a substrate, capillaries which are chemically modified differently from each other are respectively embedded in the grooves, fluid can be supplied to the plurality of embedded capillaries and detection data can be acquired (patent document 2).

Patent documents 3 to 6 disclose structures and producing methods of other microchemical chips of this kind.

PRIOR ART DOCUMENTS

Patent Documents

[Patent Document 1] Japanese Patent Publication No. 4073023
[Patent Document 2] Japanese Utility Model Registration No. 3116709
[Patent Document 3] Japanese Patent Application Laid-open No. 2000-93816
[Patent Document 4] Japanese Patent Application Laid-open No. 2001-157855
[Patent Document 5] Japanese Patent Application Laid-open No. 2000-81406
[Patent Document 6] Japanese Translation of PCT International Application Laid-open No. 2005-510695

SUMMARY OF THE INVENTION

Problem to be Solved by the Invention

According to a fine space reaction using a microchemical chip, an amount of samples to be used can be reduced to a very small level and not only that, reaction speed and reaction efficiency can be enhanced.

However, to make use of this feature, high machining technique is required, and it is difficult to inexpensively obtain a high performance microchemical chip.

Especially, to precisely realize the fine space reaction, it is necessary to reliably fix a reagent and to that end, it is preferable that an angle portion is formed on a cross section of a sample flow path.

To form the angle portion on the cross section of the sample flow path, the present applicant used a capillary as disclosed in patent documents 1 and 2, but there is a limit to easily carry out the producing method.

Hence, it is an object of the present invention to provide, as a sample flow path, a microchemical chip capable of producing, using a simple method, a square hollow groove including an angle having one piece of about 100 microns.

It is another object of the invention to provide, by one microchemical chip, many kinds of microchemical reaction fields which can easily introduce sample solution into a sample flow path.

Means for Solving the Problem

A first aspect of the present invention provides a microchemical chip, wherein the microchemical chip comprises a first substrate including a sample introducing port, a second substrate including a sample flow path, and a third substrate including a sample discharging port, the sample introducing port is formed as a hole penetrating a face and a back of the first substrate, the sample flow path is formed as a slit penetrating a face and a back of the second substrate, the sample discharging port is formed as a hole penetrating a face and a back of the third substrate, the second substrate is disposed between the first substrate and the third substrate, the sample introducing port and the sample discharging port are in communication with each other through the sample flow path, and one of ends of the sample flow path is an opening port.

According to a second aspect of the invention, in the microchemical chip according to the first aspect, the other end of the sample flow path is also an opening port.

According to a third aspect of the invention, in the microchemical chip according to the first or second aspect, the second substrate includes at least one more sample flow path, and the sample introducing port and the sample discharging port are disposed at an intersecting position of the plurality of sample flow paths.

According to a fourth aspect of the invention, in the microchemical chip of the third aspect, the plurality of sample flow paths are radially formed around the sample introducing port.

According to a fifth aspect of the invention, in the microchemical chip of any one of the first to fourth aspects, the first substrate or the second substrate is made of translucent material.

A sixth aspect of the invention provides a producing method of the microchemical chip of any one of the first to fifth aspects, the method includes a first step of disposing the first substrate including the sample introducing port, the second substrate including the sample flow path, and the third substrate including the sample discharging port at a position where the sample introducing port and the sample discharging port are in communication with each other through the sample flow path, and pasting the first to third substrates on one another, and a second step of cutting out, after the first step, the first substrate, the second substrate and the third substrate such that the end of the sample flow path becomes the opening port.

According to a seventh aspect of the invention, in the producing method of the microchemical chip of the sixth aspect, in the second step, the substrates are cutout such that lengths from the opening ports of the sample flow paths to the sample introducing port become equal to each other.

According to an eighth aspect of the invention, in the producing method of the microchemical chip of the sixth or seventh aspect, the method further includes a step of, after the second step, introducing reagents from the opening ports of the sample flow paths by capillary action, and of fixing the different reagents to the respective sample flow paths.

A ninth aspect of the invention provides a method for using the microchemical chip of any one of the first to fifth aspects, the reagent is previously fixed to the sample flow path, and sample solution is brought into contact with the sample introducing port, thereby introducing the sample solution into the sample flow path by capillary action.

According to a tenth aspect of the invention, in the method for using the microchemical chip of the ninth aspect, the reagents are introduced from the opening ports of the sample flow paths by capillary action, and the different reagents are fixed to the respective sample flow paths.

An eleventh aspect of the invention provides a method for using the microchemical chip of any one of the second to fifth aspects, selective matrixes are previously fixed to the respective sample flow paths, and sample solution including enzyme corresponding to the selective matrix is brought into contact with the sample introducing port, thereby measuring enzyme activity.

A twelfth aspect of the invention provides a method for using the microchemical chip of any one of the second to fifth aspects, selective primers are previously fixed to the respective sample flow paths, and a gene amplifying reagent and a mold DNA are brought into contact with the sample introducing port as sample solution, thereby detecting gene specific nature.

A thirteenth aspect of the invention provides a method for using the microchemical chip of any one of the first to fifth aspects, after the sample is introduced, the sample flow path is oil-sealed.

A fourteenth aspect of the invention provides a container for exclusive use for the method for using the microchemical chip of the thirteenth aspect, the microchemical chip is placed on the container, and mineral oil used as the oil sealing can be added.

According to a fifteenth aspect, in the container for exclusive use for the microchemical chip of the fourteenth aspect, metal or silicon, or both of them are used for controlling a reaction temperature of the microchemical chip.

Effect of the Invention

According to the present invention, the sample flow path is formed as the slip penetrating the face and the back of the second substrate, and the slit is sandwiched between the first substrate and the third substrate to constitute the sample flow path. Therefore, it is possible to obtain the sample flow path of a square hollow groove having an angle portion. Further, since the one end of the sample flow path is the opening port, sample solution can flow from the sample introducing port to the opening port.

EXPLANATION OF SYMBOLS

Figure 1:
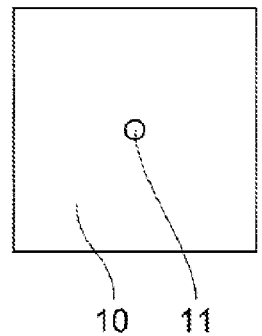
FIG. 1(a) is a diagram showing a first substrate of a microchemical chip according to an embodiment of the present invention.
FIG. 1(b) is a diagram showing a second substrate of the microchemical chip.
FIG. 1(c) is a diagram showing a third substrate of the microchemical chip.
FIG. 1(d) is a diagram showing a first step of a producing method of the microchemical chip.
FIG. 1(e) is a diagram showing a second step of the producing method of the microchemical chip.
FIG. 1(f) is a diagram showing a microchemical chip which is completed after the second step and FIG. 1(g) is a sectional view taken along a line X-X in FIG. 1(f)
Figure 1:
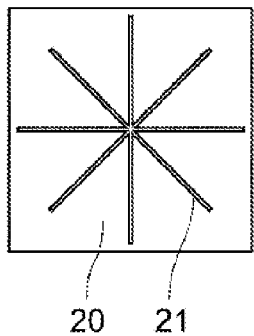
Figure 1:
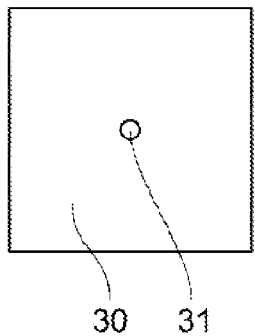
Figure 1:
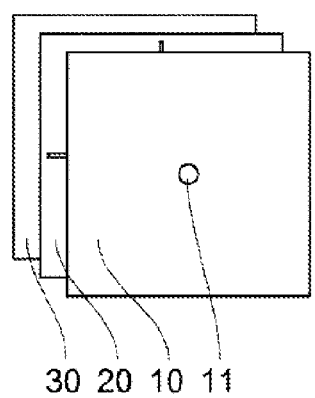
Figure 1:
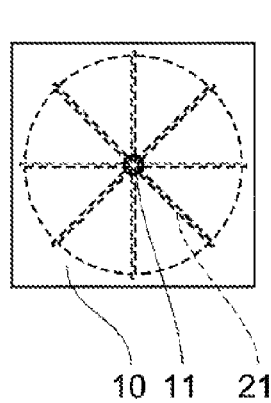
Figure 1:
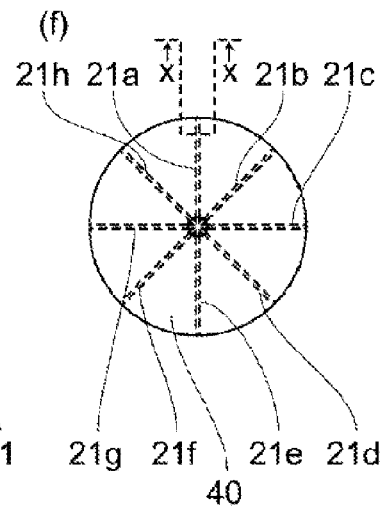
Figure 1:
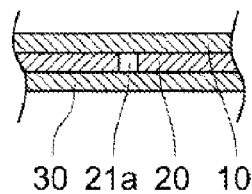

10 first substrate
11 sample introducing port
20 second substrate
21 sample flow path
21a, 21b, 21c, 21d, 21e, 21f, 21g and 21h sample flow path
30 third substrate
31 sample discharging port
40 microchemical chip

MODE FOR CARRYING OUT THE INVENTION

A first aspect of the present invention provides a microchemical chip, wherein the microchemical chip comprises a first substrate including a sample introducing port, a second substrate including a sample flow path, and a third substrate including a sample discharging port, the sample introducing port is formed as a hole penetrating a face and a back of the first substrate, the sample flow path is formed as a slit penetrating a face and a back of the second substrate, the sample discharging port is formed as a hole penetrating a face and a back of the third substrate, the second substrate is disposed between the first substrate and the third substrate, the sample introducing port and the sample discharging port are in communication with each other through the sample flow path, and one of ends of the sample flow path is an opening port. According to this aspect, the sample flow path is formed as the slip penetrating the face and the back of the second substrate, and the slit is sandwiched between the first substrate and the third substrate to constitute the sample flow path. Therefore, it is possible to obtain the sample flow path of a square hollow groove having an angle portion. Further, since the one end of the sample flow path is the opening port, sample solution can flow from the sample introducing port to the opening port.

According to a second aspect of the invention, in the microchemical chip according to the first aspect, the other end of the sample flow path is also an opening port. According to this aspect, two sample flow paths can be formed by one slit. Since the different reagents are fixed to the respective sample flow paths, a plurality of microchemical reaction fields can be formed. Since the same reagents are fixed, even if a deficiency is generated in one of the sample flow paths, it is possible to reliably detect the deficiency.

According to a third aspect of the invention, in the microchemical chip according to the first or second aspect, the second substrate includes at least one more sample flow path, and the sample introducing port and the sample discharging port are disposed at an intersecting position of the plurality of sample flow paths. According to this aspect, many sample flow paths can be formed, and since the different reagents are fixed to the respective sample flow paths, the plurality of microchemical reaction fields can be formed. By fixing the same reagent, even if a deficiency is generated in one of the sample flow paths, it is possible to reliably detect the deficiency.

According to a fourth aspect of the invention, in the microchemical chip of the third aspect, the plurality of sample flow paths are radially formed around the sample introducing port. According to this aspect, by bringing sample solution into contact with the sample introducing port, the sample solution can be made to flow into the respective sample flow paths by capillary action.

According to a fifth aspect of the invention, in the microchemical chip of any one of the first to fourth aspects, the first substrate or the second substrate is made of translucent material. According to this aspect, it is possible to detect fluorescence and luminous phenomenon.

A sixth aspect of the invention provides a producing method of the microchemical chip of any one of the first to fifth aspects, the method includes a first step of disposing the first substrate including the sample introducing port, the second substrate including the sample flow path, and the third substrate including the sample discharging port at a position where the sample introducing port and the sample discharging port are in communication with each other through the sample flow path, and pasting the first to third substrates on one another, and a second step of cutting out, after the first step, the first substrate, the second substrate and the third substrate such that the end of the sample flow path becomes the opening port. According to this aspect, after the first substrate, the second substrate and the third substrate are pasted to one another, the first substrate, the second substrate and the third substrate are cut out such that the end of the sample flow path becomes the opening port. Therefore, it is possible to reliably position the sample introducing port, the sample discharging port and the sample flow path without affecting the slit shape.

According to a seventh aspect of the invention, in the producing method of the microchemical chip of the sixth aspect, in the second step, the substrates are cutout such that lengths from the opening ports of the sample flow paths to the sample introducing port become equal to each other. According to this aspect, the sample solution can smoothly flow through the respective sample flow paths by capillary action.

According to an eighth aspect of the invention, in the producing method of the microchemical chip of the sixth or seventh aspect, the method further includes a step of, after the second step, introducing reagents from the opening ports of the sample flow paths by capillary action, and of fixing the different reagents to the respective sample flow paths. According to this aspect, the reagents are introduced from the opening ports of the sample flow paths, different reagents can be introduced.

A ninth aspect of the invention provides a method for using the microchemical chip of any one of the first to fifth aspects, the reagent is previously fixed to the sample flow path, and sample solution is brought into contact with the sample introducing port, thereby introducing the sample solution into the sample flow path by capillary action. According to this aspect, sample solution can smoothly be introduced to the respective sample flow paths.

According to a tenth aspect of the invention, in the method for using the microchemical chip of the ninth aspect, the reagents are introduced from the opening ports of the sample flow paths by capillary action, and the different reagents are fixed to the respective sample flow paths. According to this aspect, different reagents can be introduced, and sample solution can smoothly be introduced to the respective sample flow paths.

An eleventh aspect of the invention provides a method for using the microchemical chip of any one of the second to fifth aspects, selective matrixes are previously fixed to the respective sample flow paths, and sample solution including enzyme corresponding to the selective matrix is brought into contact with the sample introducing port, thereby measuring enzyme activity. According to this aspect, different kinds of enzyme reactions can simultaneously be measured.

A twelfth aspect of the invention provides a method for using the microchemical chip of any one of the second to fifth aspects, selective primers are previously fixed to the respective sample flow paths, and a gene amplifying reagent and a mold DNA are brought into contact with the sample introducing port as sample solution, thereby detecting gene specific nature. According to this aspect, many kinds of gene specific natures can simultaneously be detected.

A thirteenth aspect of the invention provides a method for using the microchemical chip of any one of the first to fifth aspects, after the sample is introduced, the sample flow path is oil-sealed. According to this aspect, it is possible to prevent a sample introduced into the sample flow path from drying.

A fourteenth aspect of the invention provides a container for exclusive use for the method for using the microchemical chip of the thirteenth aspect, the microchemical chip is placed on the container, and mineral oil used as the oil sealing can be added. According to this aspect, it is possible to reliably oil-seal the sample flow path of the microchemical chip.

According to a fifteenth aspect, in the container for exclusive use for the microchemical chip of the fourteenth aspect, metal or silicon, or both of them are used for controlling a reaction temperature of the microchemical chip. According to this aspect, since the thermal conductivity is excellent, it is easy to control a reaction temperature.

EMBODIMENTS

An embodiment of a producing method of a microchemical chip of the present invention will be described below.

FIG. 1(a) shows a first substrate of the microchemical chip of the invention. FIG. 1(b) shows a second substrate of the microchemical chip. FIG. 1(c) shows a third substrate of the microchemical chip.

The first substrate 10 includes a sample introducing port 11, the second substrate 20 includes sample flow paths 21 and the third substrate 30 includes a sample discharging port 31. The first substrate 10, the second substrate 20 and the third substrate 30 are made of glass or plastic. Silica glass can be used as the glass but other glass or synthetic resin can also be used. At least one of the first substrate 10 and the third substrate 30 is made of translucent material, and it is preferable that the translucent material is transparent material.

In a step before pasting, the first substrate 10, the second substrate 20 and the third substrate 30 have perfect square or rectangular shapes which are larger than their completed states. In this stage, it is not absolutely necessary that the first substrate 10, the second substrate 20 and the third substrate 30 have the same outer shapes, but in order to adjust their positions at the time of a pasting operation, these substrates have common shapes so that any one side, preferably two sides can be set as reference positions.

The sample introducing port 11 is formed as a hole penetrating a face and a back of the first substrate 10. The sample flow paths 21 are formed as slits penetrating a face and a back of the second substrate 20. The sample discharging port 31 is formed as a hole penetrating a face and a back of the third substrate 30. In this embodiment, four slits form a large number of sample flow paths 21, and the four slits intersect with each other at a central portion, and they are disposed at equal distances from one another. It is preferable that a hole diameter of the sample discharging port 31 is the same as that of the sample introducing port 11, hole diameters of the sample discharging port 31 and the sample introducing port 11 are larger than a width of the slit, and are larger than an opening formed at the intersection position of the slits.

FIG. 1(d) shows a first step of the producing method of the microchemical chip of the embodiment. In the first step, the first substrate 10, the second substrate 20 and the third substrate 30 are disposed and pasted on one another at a position where the sample introducing port 11 and the sample discharging port 31 are in communication with each other through the sample flow path 21. The second substrate 20 is disposed between the first substrate 10 and the third substrate 30. When they are pasted, slit intersection positions of the sample introducing port 11, the sample discharging port 31 and the sample flow path 21 match with each other.

FIG. 1(e) shows a second step of the producing method of the microchemical chip of the embodiment. In the second step, the pasted first substrate 10, the second substrate 20 and the third substrate 30 are cut out. This second step is carried out after the first step.

The first substrate 10, the second substrate 20 and the third substrate 30 are cut out, in the second step, into such shape and size that an end of each of the sample flow paths 21 becomes an opening port. In this embodiment, they are cut out into circle shapes centering on the slit intersection position so that both ends of all of the sample flow paths 21 become opening ports.

FIG. 1(f) shows a microchemical chip which is completed after the second step.

In the microchemical chip 40 of the embodiment, eight flow paths 21a, 21b, 21c, 21d, 21e, 21f, 21g and 21h are formed around the sample introducing port 11 and the sample discharging port 31.

The eight sample flow paths 21a, 21b, 21c, 21d, 21e, 21f, 21g and 21h are radially disposed at the same lengths around the sample introducing port 11 and the sample discharging port 31, and outer peripheral ends of the sample flow paths are opening ports.

FIG. 1(g) is a sectional view taken along a line X-X in FIG. 1(f).

As shown in the drawing, the sample flow path 21a is a square hollow groove having four angle portions by the first substrate 10 and the third substrate 30. By forming the sharp (not rounded) four angle portions, it is possible to reliably fix a reagent to the sample flow path 21a.

A diameter of an outer shape of the microchemical chip 40 according to the embodiment is about 10 mm, hole diameters of the sample introducing port 11 and the sample discharging port 31 are about 0.3 mm to 0.5 mm, and one sides of the sample flow paths 21a, 21b, 21c, 21d, 21e, 21f, 21g and 21h are about 0.1 mm.

Slit widths (plate thickness of second substrate 20) of the sample flow paths 21a, 21b, 21c, 21d, 21e, 21f, 21g and 21h are set greater than slit widths. According to this configuration, it is possible to reliably determine the microchemical chip 40 even if the fluorescence reaction is weak. Here, when the slit depths of the sample flow paths 21a, 21b, 21c, 21d, 21e, 21f, 21g and 21h are made greater than the slit widths, it is preferable that the slit depth is in a range of 0.1 mm to 5 mm, and the slit width is in a range of 0.02 mm to 0.2 mm.

Figure 2:
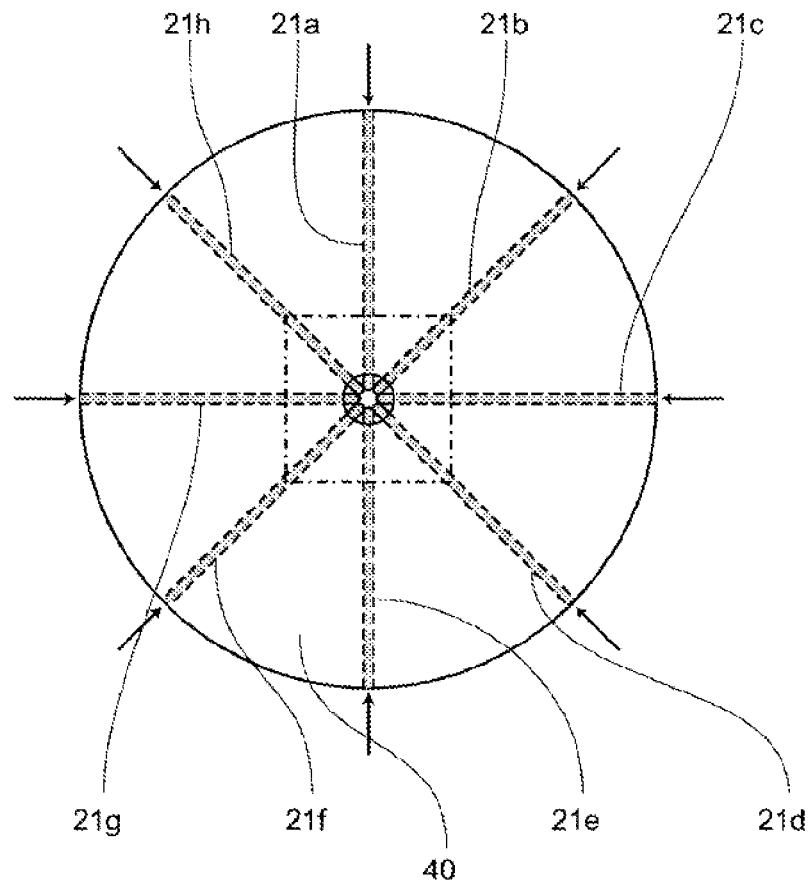
FIG. 2(a) is a plan view of a microchemical chip of the embodiment when a reagent is fixed and FIG. 2(b) is an enlarged view of essential portions of the microchemical chip.
Figure 2:
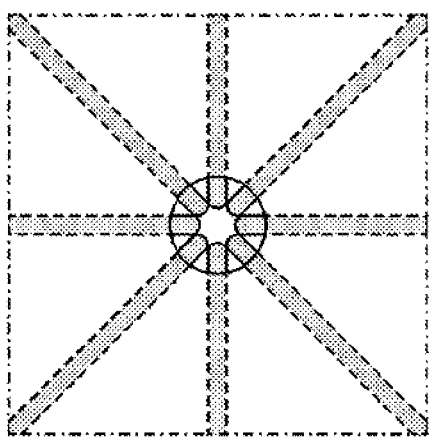

FIG. 2 show a fixing method of a reagent to the microchemical chip of the embodiment, wherein FIG. 2(a) is a plan view of the microchemical chip and FIG. 2(b) is an enlarged view of essential portions of the microchemical chip.

Reagents are introduced from the opening ports of the sample flow paths 21a, 21b, 21c, 21d, 21e, 21f, 21g and 21h by capillary action.

That is, if reagents are brought into contact with the opening ports of the sample flow paths 21a, 21b, 21c, 21d, 21e, 21f, 21g and 21h, the reagents actively flow into the sample flow paths 21a, 21b, 21c, 21d, 21e, 21f, 21g and 21h by capillary action, and the sample flow paths 21a, 21b, 21c, 21d, 21e, 21f, 21g and 21h are reliably filled with the reagents by surface tension acting at ends facing the sample introducing port 11 and the sample discharging port 31.

FIG. 2(b) shows a state where the ends face the sample introducing port 11 and the sample discharging port 31 in the sample flow paths 21a, 21b, 21c, 21d, 21e, 21f, 21g and 21h.

If the reagents are dried in a state where the sample flow paths 21a, 21b, 21c, 21d, 21e, 21f, 21g and 21h are filled with the reagents, the reagents are fixed to the four angle portions of the square hollow groove.

It is also possible to introduce different reagents into the sample flow paths 21a, 21b, 21c, 21d, 21e, 21f, 21g and 21h and fixed the reagents therein. In this case, reagents may be introduced into the sample flow path 21a, the sample flow path 21b, and the sample flow path 21c in the order, or different reagents may be introduced into all of the sample flow paths 21a, 21b, 21c, 21d, 21e, 21f, 21g and 21h at the same time, and after the reagents are introduced into all of the sample flow paths 21a, 21b, 21c, 21d, 21e, 21f, 21g and 21h, and the reagents are fixed by drying.

If an appropriate matrix is used and appropriate viscosity is given to the reagents, it is possible to avoid uneven density of reagents in the sample flow paths 21a, 21b, 21c, 21d, 21e, 21f, 21g and 21h. Here, as the matrix, it is possible to use any of polyethylene glycol, glycerol, polysaccharide, protein, surface-active agent and inorganic salt or a mixture thereof within such a range that reaction thereafter is not influenced.

Figure 3:
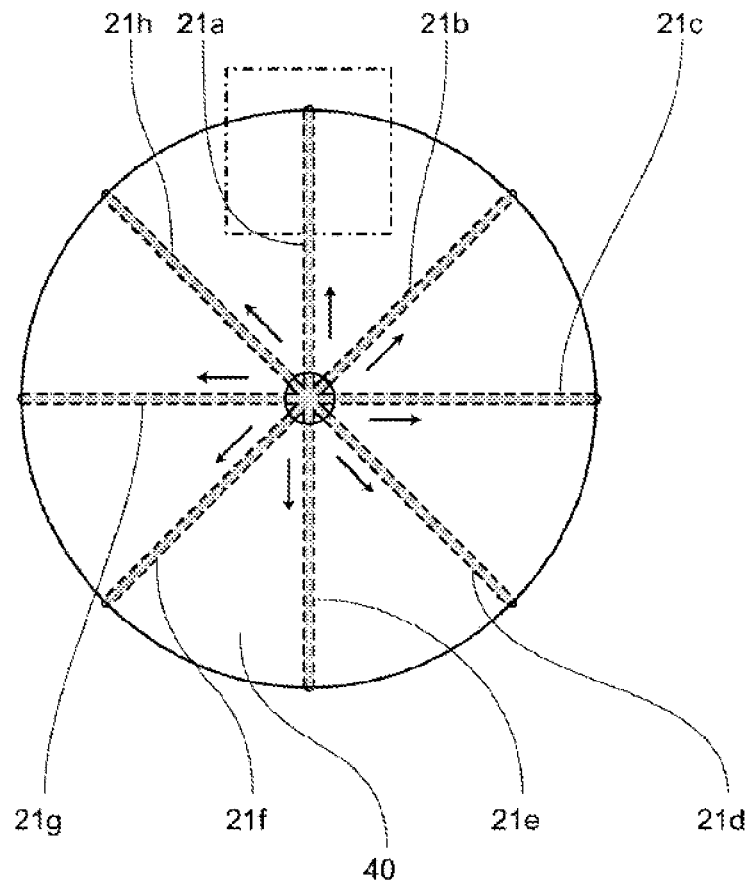
FIG. 3(a) is a plan view when the microchemical chip of the embodiment is used and FIG. 3(b) is an enlarged view of essential portions of the microchemical chip.
Figure 3:
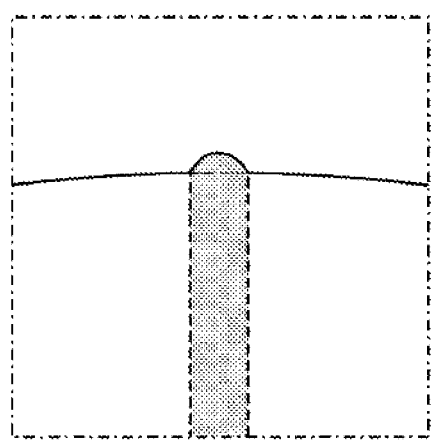

FIG. 3 show a method for using the microchemical chip of the embodiment, wherein FIG. 3(a) is a plan view of the microchemical chip and FIG. 3(b) is an enlarged view of essential portions of the microchemical chip.

Sample solution is introduced from the sample introducing port 11 by capillary action.

That is, if the sample solution is brought into contact with the sample introducing port 11, the sample solution actively flows into the sample flow paths 21a, 21b, 21c, 21d, 21e, 21f, 21g and 21h by the capillary action, and the sample flow paths 21a, 21b, 21c, 21d, 21e, 21f, 21g and 21h are reliably filled with the sample solution by surface tension acting in the opening ports of the sample flow paths 21a, 21b, 21c, 21d, 21e, 21f, 21g and 21h.

FIG. 3(b) shows a state at the opening port in the sample flow path 21a.

If the sample solution is introduced into the sample flow paths 21a, 21b, 21c, 21d, 21e, 21f, 21g and 21h, gas is sprayed into the sample introducing port 11, thereby discharging sample solution existing in the sample introducing port 11 from the sample discharging port 31.

A reagent which is already fixed dissolves into the sample solution introduced into the sample flow paths 21a, 21b, 21c, 21d, 21e, 21f, 21g and 21h, the sample solution and the reagent are mixed together, and if they are managed under appropriate temperature condition, reaction of the sample and the reagent is started.

Here, a detecting method of reaction between the sample and the reagent will be described.

If fluorescence is emitted as the reaction proceeds, fluorescence is detected, if light is chemically emitted as the reaction proceeds, photon is detected, and if color is emitted as the reaction proceeds, absorbance is detected. As a detecting method of reaction, many other general detection methods can be used.

When various kinds of reactions are carried out using the microchemical chip of the embodiment, temperature control and an environment which prevents solution from drying are preferable, and oil sealing can be conceived for example.

An oil sealing method using a dish for exclusive use is more preferable.

To control a temperature of the microchemical chip of the embodiment, it is possible to use a dish (container) for exclusive use. It is preferable that the dish for exclusive use is made of material having excellent thermal conductivity, copper is preferable as metal, and silicon material is also suitable. If a bottom surface of the dish for exclusive use is appropriately machined, i.e., if the bottom surface of the dish is formed into a concave-convex surface to bring the dish for exclusive use and a circular multi-flow path chip into contact with each other, temperature control becomes easy.

If a center surface and an outer peripheral surface of the flow path are closed with mineral oil (oil sealing) after sample is introduced into the microchemical chip, it is possible to prevent an interior of the flow path from drying.

That is, if the circular multi-flow path chip is placed on the dish for exclusive use after the sample is introduced and a small amount of mineral oil is added, both ends of the flow path formed in the microchemical chip can be closed with mineral oil.

Since solution in the oil-sealed flow path can not be vaporized at a boiling point or lower, even if the temperature change is repeated, the interior of the flow path does not dry.

Detection of human papillomavirus using the microchemical chip will be described below.

As human papillomavirus that causes cervical cancer, there are one having high cancer risk and one having low cancer risk. To prevent the infection of cervical cancer, it is important not only to know whether a person is infected with the virus or not but also to know its infection type. Various viruses have a common gene sequence portion and a gene sequence portion which is particular to that subspecies. Therefore, if a characteristic gene portion of the virus is amplified, it is possible to determine whether the person is infected with target virus.

Hence, if selective amplification of gene is simultaneously carried out for kind of subspecies of human papillomavirus in each of the flow paths, it is possible to collectively and simultaneously determine which type the injection virus is or which type the non-injected virus is.

In an experiment, a human papillomavirus detecting kit (TAKARA code 6602) was used.

Solution of a primer which selectively amplified type 16 of human papillomavirus, solution of a primer which selectively amplified type 18 of human papillomavirus, and solution of a primer which selectively amplified type 33 of human papillomavirus were introduced, by capillary action, from outer peripheral surfaces of flow paths of a circular multi-flow path chip, and they were dried one night at 65° C., thereby fixing the primers to interiors of the flow paths. Two microliters of PCR reaction solution by heat-resistant DNA polymerase in which an appropriate amount of ethidium bromide or SYBR Green including a mold were made to fall in drops into a sample introducing portion of the circular multi-flow path chip, and the sample was uniformly introduced from center surfaces of the flow paths into the flow paths by capillary action. After the sample was introduced, the circular flow path chip was placed on a copper dish, and mineral oil of such an amount that the entire flow paths sank therein was added, thereby oil-sealing the flow paths.

The copper dish was placed on an aluminum block, and a temperature of the aluminum block was changed, thereby adjusting a temperature of the chip. That is, the aluminum block was heated to 95° C. and after 15 seconds were elapsed, the aluminum block was cooled to 57° C., and 45 seconds were allowed to elapse. This operation was carried out 20 times, and fluorophore which is proportional to an amount of amplified double-stranded DNA was amplified only in a combination of primers which match with a mold which is to be modified in reaction solution.

As another example, it is also possible to detect protease activity.

If selective matrix is previously fixed to each of sample flow paths of the microchemical chip and sample solution including enzyme corresponding to the selective matrix is brought into contact with the sample introducing port, it is possible to measure enzyme activity.

Further, if a selective primer is previously fixed to each of sample flow paths of the microchemical chip and a gene amplifying reagent and a mold DNA are brought into contact with sample introducing port as sample solution, it is possible to detect gene specific nature.

Figure 4:
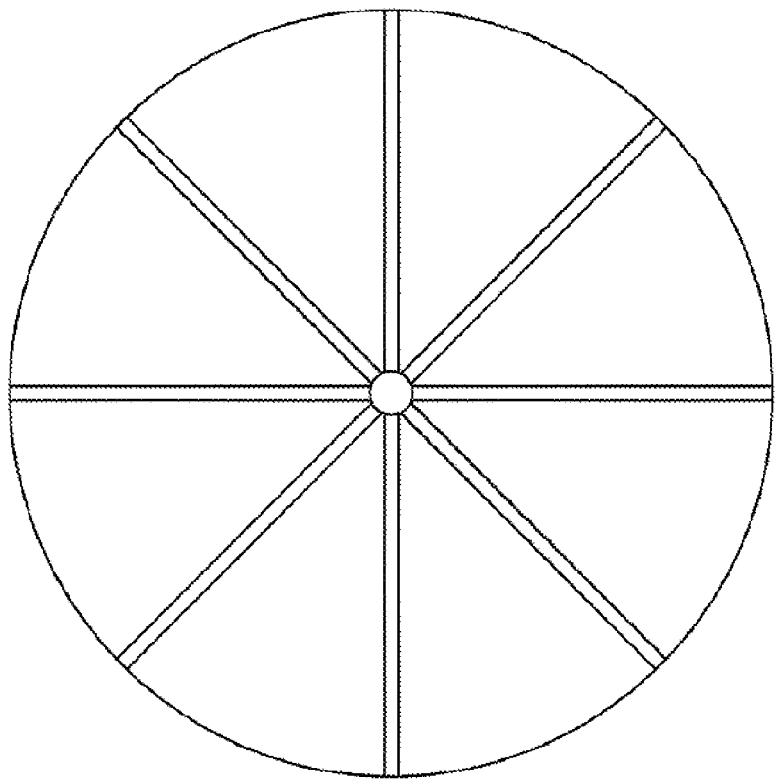
FIG. 4(a) is a plan view showing an outward appearance of the microchemical chip of the embodiment and FIG. 4(b) is a front view of the microchemical chip.
Figure 4:
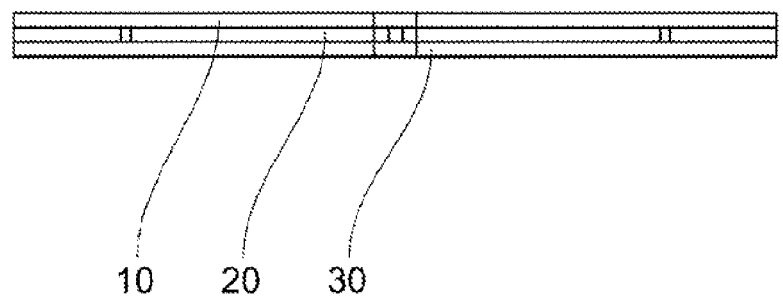

FIG. 4 show an outward appearance of the microchemical chip of the embodiment, wherein FIG. 4(a) is a plan view thereof and FIG. 4(b) is a front view thereof. A bottom view is the same as the plan view. A right side view, a left side view and a rear view are the same as the front view. The first substrate 10 or the third substrate 30 is made of translucent material, preferably transparent material. Preferably, all of the first substrate 10, the second substrate 20 and the third substrate 30 are made of translucent material, preferably transparent material.

Figure 5:
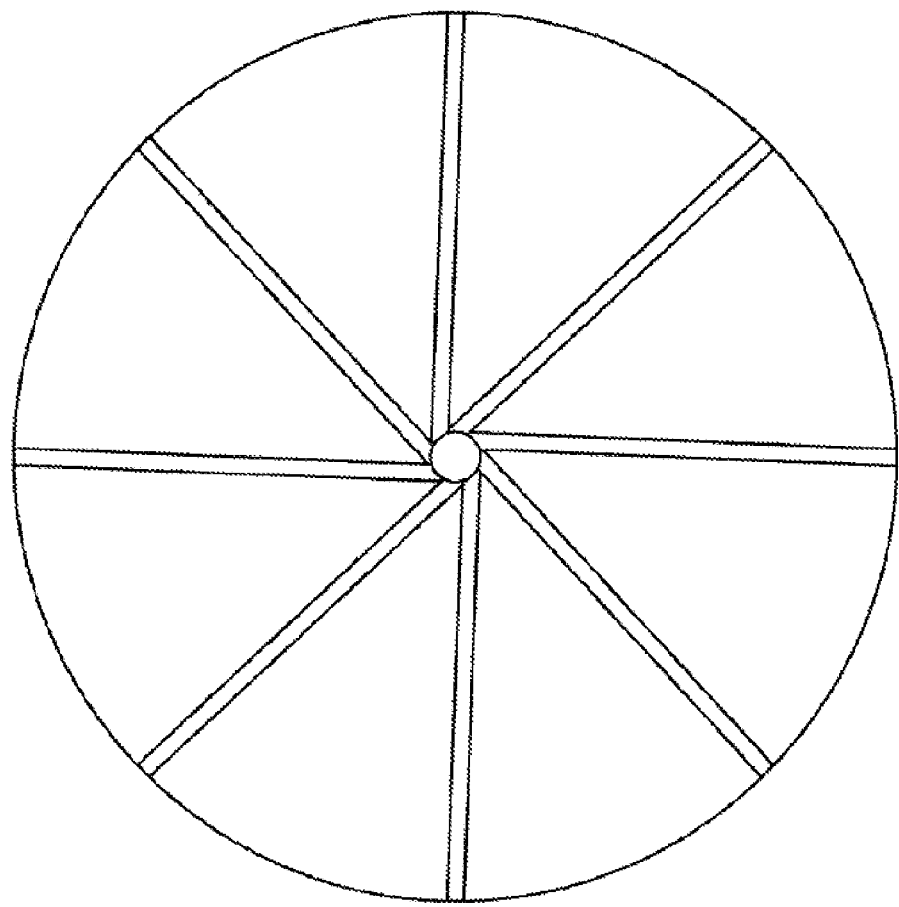
FIG. 5(a) is a plan view showing an outward appearance of another embodiment of the invention and FIG. 5(b) is a front view of the microchemical chip.
Figure 5:
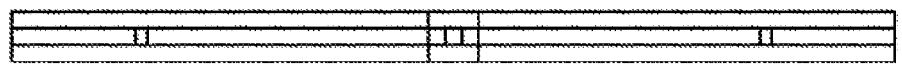

FIG. 5 show an outward appearance of the microchemical chip of another embodiment, wherein FIG. 5(a) is a plan view thereof and FIG. 5(b) is a front view thereof. A bottom view is the same as the plan view. A right side view, a left side view and a rear view are the same as the front view. The first substrate 10 or the third substrate 30 is made of translucent material, preferably transparent material. Preferably, all of the first substrate 10, the second substrate 20 and the third substrate 30 are made of translucent material, preferably transparent material.

Figure 6:
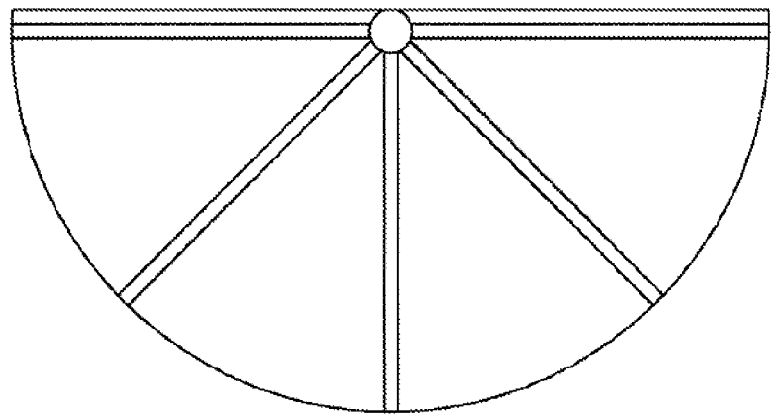
FIG. 6(a) is a plan view showing an outward appearance of another embodiment of the invention.
FIG. 6(b) is a front view of the microchemical chip.
FIG. 6(c) is a right side view of the microchemical chip and FIG. 6(d) is a rear view of the microchemical chip.
Figure 6:
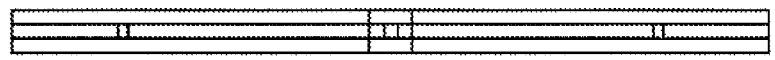
Figure 6:
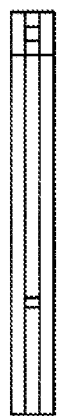
Figure 6:
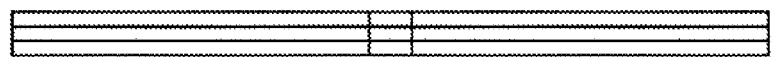

FIG. 6 show an outward appearance of the microchemical chip of another embodiment, wherein FIG. 6(a) is a plan view thereof, FIG. 6(b) is a front view thereof, FIG. 6(c) is a right side view thereof and FIG. 6(d) is a rear view thereof. A left side view is the same as the right side view. A bottom view and the plan view are symmetric. The first substrate 10 or the third substrate 30 is made of translucent material, preferably transparent material. Preferably, all of the first substrate 10, the second substrate 20 and the third substrate 30 are made of translucent material, preferably transparent material.

Figure 7:
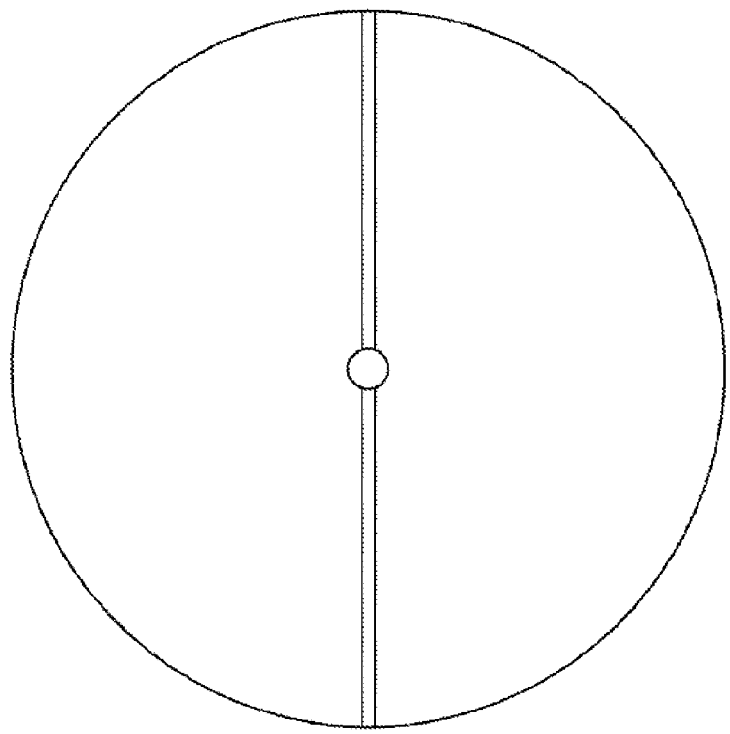
FIG. 7(a) is a plan view showing an outward appearance of another embodiment of the invention.
FIG. 7(b) is a front view of the microchemical chip and FIG. 7(c) is a right side view of the microchemical chip.
Figure 7:
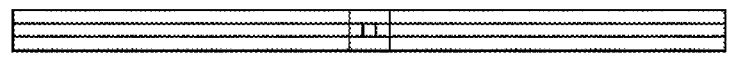
Figure 7:

FIG. 7 show an outward appearance of the microchemical chip of another embodiment, wherein FIG. 7(a) is a plan view thereof, FIG. 7(b) is a front view thereof and FIG. 7(c) is a right side view thereof. A bottom view is the same as the plan view, a left side view is the same as the right side view, and a rear view is the same as the front view. The first substrate 10 or the third substrate 30 is made of translucent material, preferably transparent material. Preferably, all of the first substrate 10, the second substrate 20 and the third substrate 30 are made of translucent material, preferably transparent material.

Figure 8:
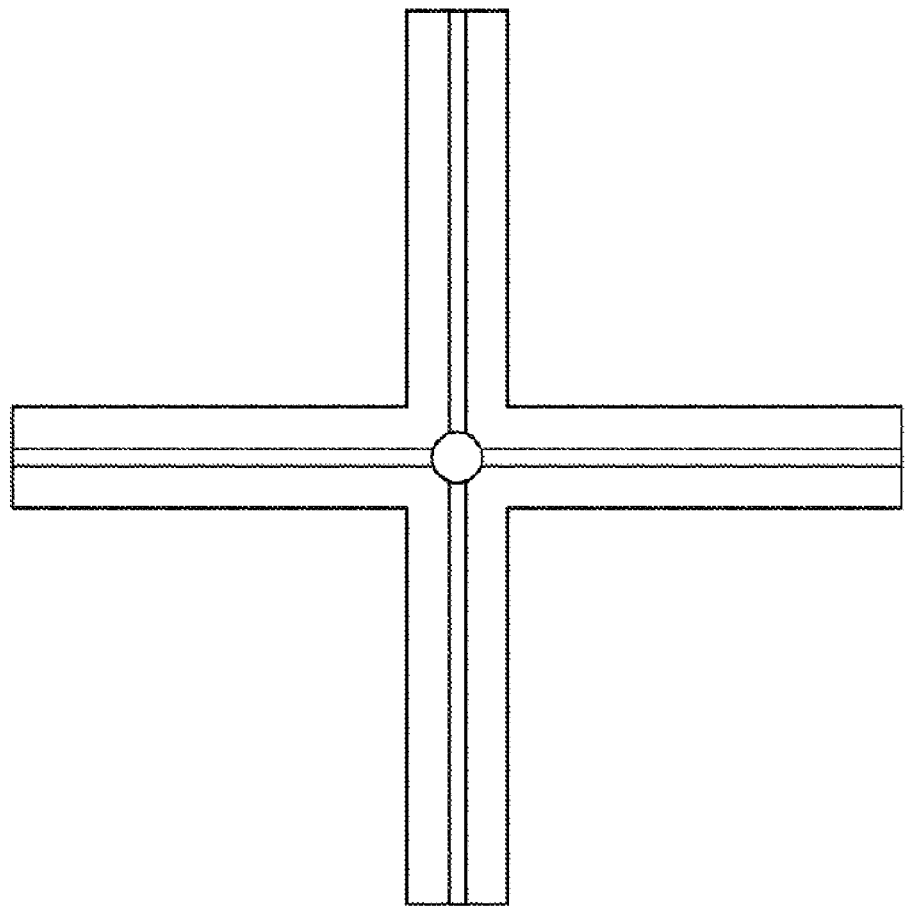
FIG. 8(a) is a plan view showing an outward appearance of another embodiment of the invention and FIG. 8(b) is a front view of the microchemical chip.
Figure 8:
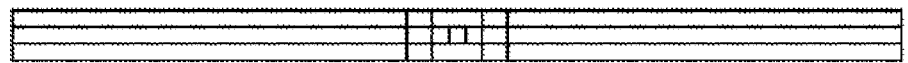

FIG. 8 show an outward appearance of the microchemical chip of another embodiment, wherein FIG. 8(a) is a plan view thereof and FIG. 8(b) is a front view thereof. A bottom view is the same as the plan view. A right side view, a left side view and a rear view are the same as the front view. The first substrate 10 or the third substrate 30 is made of translucent material, preferably transparent material. Preferably, all of the first substrate 10, the second substrate 20 and the third substrate 30 are made of translucent material, preferably transparent material.

Figure 9:
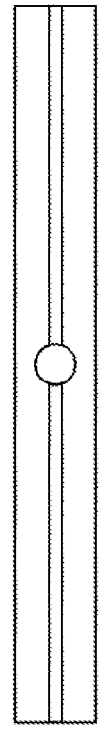
FIG. 9(a) is a plan view showing an outward appearance of another embodiment of the invention.
FIG. 9(b) is a front view of the microchemical chip and FIG. 9(c) is a right side view of the microchemical chip.
Figure 9:
Figure 9:
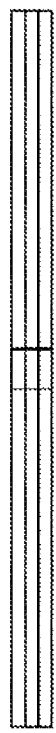

FIG. 9 show an outward appearance of the microchemical chip of another embodiment, wherein FIG. 9(a) is a plan view thereof, FIG. 9(b) is a front view thereof and FIG. 9(c) is a right side view thereof. A bottom view is the same as the plan view, a left side view is the same as the right side view, and a rear vied is the same as the front view. The first substrate 10 or the third substrate 30 is made of translucent material, preferably transparent material. Preferably, all of the first substrate 10, the second substrate 20 and the third substrate 30 are made of translucent material, preferably transparent material.

Figure 10:
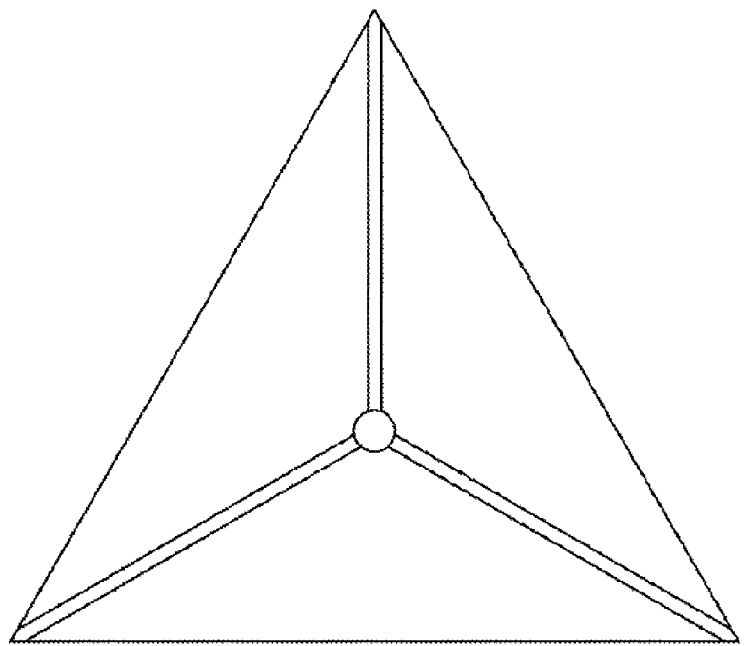
FIG. 10(a) is a plan view showing an outward appearance of another embodiment of the invention.
FIG. 10(b) is a front view of the microchemical chip and FIG. 10(c) is a right side view of the microchemical chip.
Figure 10:
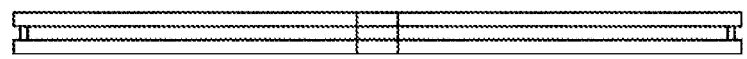
Figure 10:
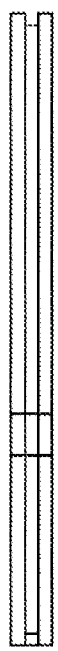

FIG. 10 show an outward appearance of the microchemical chip of another embodiment, wherein FIG. 10(a) is a plan view thereof, FIG. 10(b) is a front view thereof and FIG. 10(c) is a right side view thereof. A bottom view is the same as the plan view, a left side view is the same as the right side view, and a rear vied is the same as the front view. The first substrate 10 or the third substrate 30 is made of translucent material, preferably transparent material. Preferably, all of the first substrate 10, the second substrate 20 and the third substrate 30 are made of translucent material, preferably transparent material.

Figure 11:
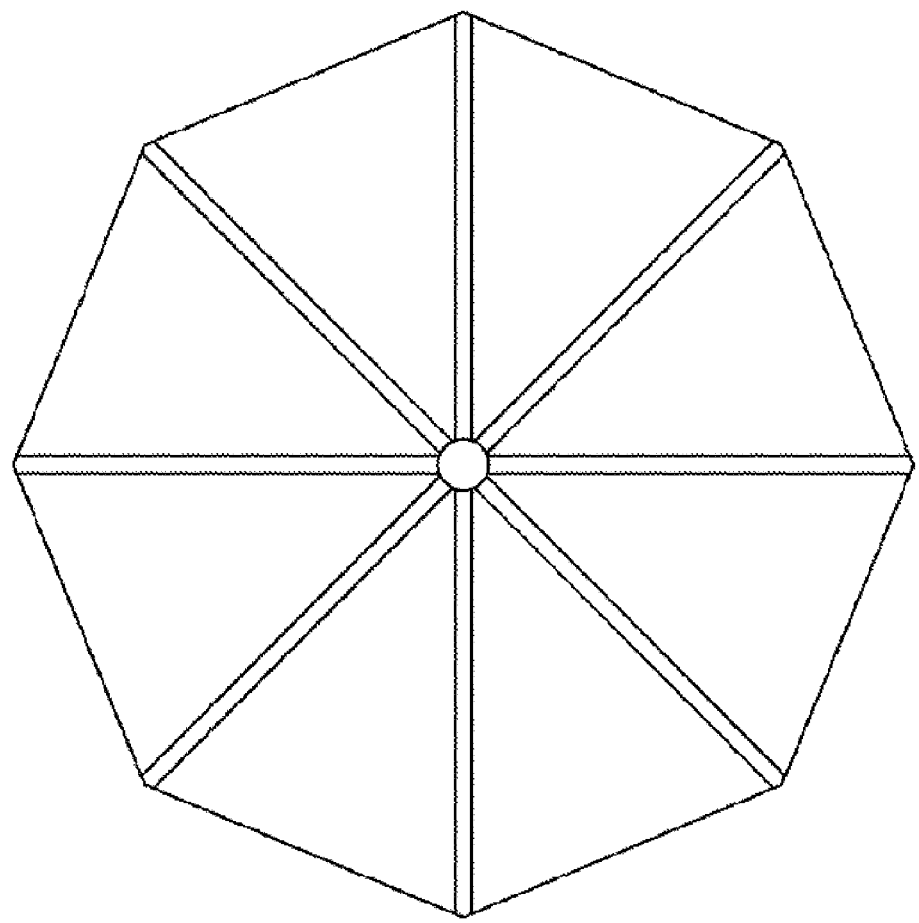
FIG. 11(a) is a plan view showing an outward appearance of another embodiment of the invention and FIG. 11(b) is a front view of the microchemical chip.
Figure 11:
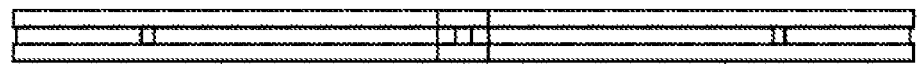

FIG. 11 show an outward appearance of the microchemical chip of another embodiment, wherein FIG. 11(a) is a plan view thereof and FIG. 11(b) is a front view thereof. A bottom view is the same as the plan view. A right view, a left side and a rear view are the same as the front view. The first substrate 10 or the third substrate 30 is made of translucent material, preferably transparent material. Preferably, all of the first substrate 10, the second substrate 20 and the third substrate 30 are made of translucent material, preferably transparent material.

INDUSTRIAL APPLICABILITY

As described above, according to the microchemical chip of the present invention, it is possible to measure a chemical/biochemical function of many items using a fine flow path formed on a substrate.

The invention claimed is:

1. A microchemical chip, wherein the microchemical chip comprises a first substrate including a sample introducing port, a second substrate including a plurality of sample flow paths, and a third substrate including a sample discharging port, the sample introducing port is formed as a hole penetrating a face and a back of the first substrate, the plurality of sample flow paths is radially formed as slits penetrating a face and a back of the second substrate, the sample discharging port is formed as a hole penetrating a face and a back of the third substrate, the second substrate is disposed between the first substrate and the third substrate, the sample introducing port and the sample discharging port are in communication with each other through the plurality of sample flow paths, and one of ends of each sample flow path is an opening port, and wherein a hole diameter of the sample discharging port and that of the sample introducing port are larger than a width of each slit in a direction perpendicular to a hole penetrating direction, and are larger than an opening formed at an intersection position of the slits, and the sample introducing port, the sample discharging port and the intersection position of the slits match with one another.

2. The microchemical chip according to claim 1, wherein the other end of each sample flow path is also an opening port.

3. The microchemical chip according to claim 1 or 2, wherein the sample introducing port and the sample discharging port are disposed at an intersecting position of the plurality of sample flow paths.

4. The microchemical chip according to claim 1, wherein the first substrate or the second substrate is made of translucent material.

5. A producing method of the microchemical chip according to claim 1, comprising a first step of disposing the first substrate including the sample introducing port, the second substrate including the sample flow path, and the third substrate including the sample discharging port at a position where the sample introducing port and the sample discharging port are in communication with each other through the sample flow path, and pasting the first to third substrates on one another, and a second step of cutting out, after the first step, the first substrate, the second substrate and the third substrate such that the end of the sample flow path becomes the opening port.

6. The producing method of the microchemical chip according to claim 5, wherein in the second step, the substrates are cut out such that lengths from the opening ports of the sample flow paths to the sample introducing port become equal to each other.

7. The producing method of the microchemical chip according to claim 5 or 6, further comprising a step of, after the second step, introducing reagents from the opening ports of the sample flow paths by capillary action, and of fixing the different reagents to the respective sample flow paths.

8. A method for using the microchemical chip according to claim 1, wherein the reagent is previously fixed to the sample flow path, and sample solution is brought into contact with the sample introducing port, thereby introducing the sample solution into the sample flow path by capillary action.

9. The method for using the microchemical chip according to claim 8, wherein the reagents are introduced from the opening ports of the sample flow paths by capillary action, and the different reagents are fixed to the respective sample flow paths.

10. A method for using the microchemical chip according to claim 2, wherein selective matrixes are previously fixed to the respective sample flow paths, and sample solution including enzyme corresponding to the selective matrix is brought into contact with the sample introducing port, thereby measuring enzyme activity.

11. A method for using the microchemical chip according to claim 2, wherein selective primers are previously fixed to the respective sample flow paths, and a gene amplifying reagent and a mold DNA are brought into contact with the sample introducing port as sample solution, thereby detecting gene specific nature.

12. A method for using the microchemical chip according to claim 1, wherein after the sample is introduced, the sample flow path is oil-sealed.

13. A container for exclusive use for the method for using the microchemical chip according to claim 12, wherein the microchemical chip is placed on the container, and mineral oil used as the oil sealing can be added.

14. The container for exclusive use for the microchemical chip according to claim 13, wherein metal or silicon, or both of them are used for controlling a reaction temperature of the microchemical chip.

* * * * *